US012797497B2

(12) United States Patent
Ozdemir

(10) Patent No.: US 12,797,497 B2
(45) Date of Patent: Nov. 17, 2026

(54) TUNNEL TYPE DISINFECTION SYSTEM

(71) Applicant: Xray Center Guvenlik Sistemleri A.S, Istanbul (TR)

(72) Inventor: Murat Ozdemir, Istanbul (TR)

(73) Assignee: Xray Center Guvenlik Sistemleri A.S, Istanbul (TR)

( * ) Notice: Subject to any disclaimer, the term of this patent is extended or adjusted under 35 U.S.C. 154(b) by 346 days.

(21) Appl. No.: 18/384,240

(22) Filed: Oct. 26, 2023

(65) Prior Publication Data

US 2024/0075175 A1 Mar. 7, 2024

Related U.S. Application Data

(63) Continuation of application No. PCT/EP2021/061285, filed on Apr. 29, 2021.

(51) Int. Cl.
*A61L 2/10* (2026.01)

(52) U.S. Cl.
CPC .................................... *A61L 2/10* (2013.01)

(58) Field of Classification Search
CPC .......... A61L 2/10; A61L 2/24; A61L 2103/23; A61L 2202/122; A61L 2202/14
USPC .................................................. 250/455.11
See application file for complete search history.

(56) References Cited

U.S. PATENT DOCUMENTS

2004/0052702 A1* 3/2004 Shuman ................ A23B 2/425 422/208
2020/0254122 A1* 8/2020 Starkweather .......... A61L 2/202
2021/0145996 A1* 5/2021 Morton ..................... A61L 2/26
2021/0299318 A1* 9/2021 Mullen ..................... A61L 2/24

* cited by examiner

*Primary Examiner* — Kiet T Nguyen
(74) *Attorney, Agent, or Firm* — Hybrid Law Group P.C.

(57) ABSTRACT

A baggage disinfection system forming a tunnel is provided. The system has a roller assembly operated by a motor that causes the roller assembly to convey objects at a rate of between about 0.10 m/second and about 0.50 m/second from an entry end of the system to an exit end of the system, such that the travel time between the entry end of the system and the exit end of the system is less than or equal to about 30 seconds. In one embodiment, the system is capable of inactivating at least 99.9% of Sars-Cov-2 viruses passing through the tunnel within the travel time. In other embodiments, the travel time is less than about 10 seconds, and the system is capable of inactivating at least 99.9% of Sars-Cov-2 or mutations thereof passing through the tunnel, or 99.99% of Sars-Cov-2 or mutations thereof passing through the tunnel.

12 Claims, 9 Drawing Sheets

TUNNEL TYPE DISINFECTION SYSTEM

BACKGROUND

This application is a continuation of International Application Serial No. PCT/EP/2021/061285, filed Apr. 29, 2021, which is incorporated by reference in its entirety.

This invention relates generally to the field of disinfection systems for disinfecting objects using UV light as they travel through a disinfecting tunnel.

As COVID-19 continues to spread and wreak havoc on lives around the world, airports, schools and other public and private buildings and facilities are considering new means of sanitation and disinfection to help curb the spread of Sars-Cov-2, its variants and other harmful pathogens. Various means have been proposed to disinfect objects entering public and private facilities, including the use of chemicals or various forms of radiation to disrupt the nucleic acid molecules of pathogens, thus inactivating them and eliminating their ability to propagate. One such means is ozone. Another means is ultraviolet C (UVC) light.

Many public places and facilities already have security systems in place to check baggage and other objects entering buildings. For example, airports, shopping malls, train stations and courthouses have x-ray security screening systems that check baggage and cargo for metal objects, guns, bombs, and other security threats. These systems are designed to enable their handlers to detect and eliminate security threats before they are able to enter their buildings, airplanes, trains, etc. However, the threat of weapons and bombs entering public buildings, airplanes, trains and other public and private spaces has been eclipsed by the threat of pathogens that are invisible, undetectable, and cause much greater and widespread destruction and death. Thus, what is needed in addition to x-ray security screening systems are means of eliminating or reducing the pathogens that enter these places, facilities, buildings and means of transportation and have the ability to cause much greater and more widespread destruction to lives and livelihoods than any weapon possibly could.

Tunnel-type baggage and cargo conveyor handling systems have been developed that claim to disinfect baggage and cargo. However, none are known or able to effectively disinfect the greatest current threats to public health and safety, such as Sars-Covid-2.

One problem or constraint is the conveyor speed of current baggage handling systems. For example, the speeds of x-ray baggage screening systems at airports are set to optimize the ability of the airport to handle the number of passengers it processes in a safe and effective manner to check for safety threats. Any baggage disinfection system implemented at an airport would have to be able to integrate with the x-ray screening systems that the airport uses and match the same speed of the x-ray system so that baggage doesn't pile up or run into each other when it gets into the x-ray screening system. X-ray screening systems at airports typically convey baggage at a rate of about 0.20 m/second. Thus, any baggage disinfection system would have to be able to handle baggage moving at that speed and be able to inactivate a sufficient percentage of pathogen in a short amount of time to be useful. The performance threshold required by the U.S. EPA is 99.9% as set forth in ASTM E1153. Thus, if company's want to market products as sanitizers, 99.9% killing of a pathogen is the required threshold. However, killing 99.9% of deadly pathogens such as SARS-Cov-2 may not be sufficient to protect public health. Although UVC light is known to inactive pathogens, an important variable in effective inactivation of at least 99.9% of pathogens is the amount of time that the pathogen is exposed to the light, and the strength of the light that reaches the pathogen. These variables have not been worked out in tunnel type baggage and cargo conveyor disinfection systems and are not obvious or determinable using theoretical calculations.

Thus, what is needed are tunnel type baggage and cargo conveyor disinfection systems that can be integrated with current x-ray screening systems and can safely, effectively and conveniently inactive at least 99.9% of harmful pathogens, including coronaviruses such as Sars-Cov-2, and preferably 99.99% of harmful pathogens, including Sars-Cov-2, found on the surface of baggage, cargo and other objects traveling through the tunnel of said disinfection systems.

Another problem exists with respect to the disinfection of letters and packages at post offices and shipping companies. Conveyor systems exist at these locations, but none that can disinfect letters and packages that pass through tunnels on conveyors at high speeds. What is needed is a tunnel type letter and package conveyor disinfection system that can effectively disinfect these materials, i.e. inactive at least 99.9% of pathogens and preferably 99.99% of pathogens, without slowing down the sorting process or slowing down the standard conveyor speeds operating within these fast conveyor systems.

SUMMARY

One object of the invention is to provide a tunnel type baggage and cargo conveyor disinfection system that is capable of inactivating 99.9% of a pathogen during the time it takes for the object to travel from an entry side of the tunnel to an exit side of the tunnel, with that time being equal to or less than 30 seconds, equal to or less than 10 seconds, equal to or less than 8 seconds, equal to or less than 7 seconds, equal to or less than 6 seconds, or equal to or less than 5 seconds. In one embodiment, the pathogen is a virus, such as an influenza virus, or a coronavirus, including without limitation, SARS, MERS and Sars-Cov-2 or their respective variants. In another embodiment, the pathogen is a bacteria or a fungus. In another embodiment, the system is capable of inactivating at least 99.99% of a coronavirus or 99.9% of a coronavirus. In one embodiment, the coronavirus is Sars-Cov-2 or a variant (sometimes referred to as a mutation) thereof.

In one exemplary embodiment, a baggage or cargo disinfection system forming a tunnel with at least twelve UVC emitting light bulbs is provided. The system has a roller assembly operated by a motor that causes the roller assembly to convey objects at a rate of between about 0.10 m/second and about 0.50 m/second from an entry end of the system to an exit end of the system, such that the travel time between the entry end of the system and the exit end of the system is equal to or less than 30 seconds, equal to or less than 10 seconds, equal to or less than 8 seconds, equal to or less than 7 seconds, equal to or less than 6 seconds, or equal to or less than 5 seconds. In one embodiment, the system has a roller assembly operated by a motor that causes the roller assembly to convey objects at a rate of about 0.20 m/second. In one embodiment, the system is capable of inactivating at least 99.9% of Sars-Cov-2 viruses (or variants) passing through the tunnel within the travel time inside the tunnel. In another embodiment, the system is capable of inactivating at least 99.99% of Sars-Cov-2 viruses (or variants) passing through the tunnel within the travel time inside the tunnel. In other embodiments, the travel time inside the tunnel is equal to or less than about 10 seconds, equal to or less than about 8 seconds, equal to or less than about 7 seconds, equal to or less than about 6 seconds or equal to or less than about 5 seconds, and the system is capable of inactivating at least 99.9% of Sars-Cov-2 viruses (or variants) passing through the tunnel within those travel times, or 99.99% of Sars-Cov-2 viruses (or variants) passing through the tunnel within those travel times. The system is capable of inactivating 99.9% or 99.99% of viruses, including influenza viruses and coronaviruses, including without limitations, SARS, MERS and Sars-Cov-2 and variants or mutations thereof within the above travel times through the tunnel.

In another exemplary embodiment, a letter, package, baggage or cargo disinfection system forming a tunnel is provided. The system has a conveyor assembly having a frame and a series of rollers attached to the frame. The frame has two or more supporting structures to support the frame and an opening on a side of the frame. The rollers are spaced apart at a predetermined distance from one another. The system further includes a motor that operates the rollers and causes them to convey objects at a rate of between about 0.10 m/second and about 0.50 m/second or alternatively a rate of between about 0.50 m/second and about 4.0 m/second from an entry end of the conveyor assembly to an exit end of the conveyor assembly. In one embodiment the motor operates the rollers and causes them to convey objects at a rate of about 0.20 m/second or alternatively at a rate of about 2.0 m/second. The system further includes a bottom drawer light bulb assembly that slides in and out of the opening on the side wall of the conveyor assembly frame. The bottom drawer light bulb assembly has a base with at least one opening containing a cooling fan and further contains at least two ultraviolet light bulbs that are oriented in the bottom drawer light bulb assembly in a direction that is perpendicular to the rollers. Each light bulb emits light at a wavelength of between about 250 nm and about 260 nm. A removable wire mesh cover is disposed above the ultraviolet light bulbs and protects them from falling objects. A tunnel frame is connected to the conveyor assembly. The tunnel frame has a roof assembly and two opposing wall assemblies that together support the roof assembly. The roof assembly has a wire mesh extending across it, and each of the two opposing wall assemblies have a wire mesh that extend across each of the opposing wall assemblies. Each of the roof assembly and two opposing wall assemblies contain a gap that extend at least a part of the distance between an entry end of the tunnel frame and an exit end of the tunnel frame. The system further includes a top drawer light bulb assembly that slides in and out of the gap in the roof assembly. The top drawer light bulb assembly contains at least two ultraviolet light bulbs that are oriented in the top drawer light bulb assembly in a direction that is perpendicular to the rollers, and each light bulb emits light at a wavelength of between about 250 nm and about 260 nm. The light bulbs are disposed above the wire mesh extending across the roof assembly, such that the wire mesh forms a protective barrier between the light bulbs and the tunnel itself. The system further includes a first side drawer light bulb assembly that slides in an out of the gap in the first of the two opposing wall assemblies. The first side drawer light bulb assembly contains at least two ultraviolet light bulbs that are oriented in said first side drawer light bulb assembly in a direction that is perpendicular to the rollers, and each light bulb emits light at a wavelength of between about 250 nm and about 260 nm. The light bulbs are disposed behind the wire mesh extending across the first opposing wall assembly, such that the wire mesh forms a protective barrier between the light bulbs and the tunnel itself. The system further includes a second side drawer light bulb assembly that slides in and out of the gap in the second of the two opposing wall assemblies. The second side drawer light bulb assembly contains at least two ultraviolet light bulbs that are oriented in said second light bulb assembly in a direction that is perpendicular to the rollers, and each light bulb emits light at a wavelength of between about 250 nm and about 260 nm. The light bulbs are disposed behind the wire mesh extending across the second opposing wall assembly, such that the wire mesh forms a protective barrier between the light bulbs and the tunnel itself. The disinfection system is capable of inactivating at least 99.9% of a pathogen passing through the tunnel in equal to or less than about 30 seconds, equal to or less than about 10 seconds, equal to or less than about 8 seconds, equal to or less than about 7 seconds, equal to or less than about 6 seconds, or equal to or less than about 5 seconds. In one embodiment, the pathogen is a coronavirus, such as SARS, MERS, or Sars-Cov-2 or variants thereof. The pathogen can also be an influenza virus or a bacteria. In another embodiment, the disinfection system is capable of inactivating at least 99.9% of a pathogen passing through the tunnel in equal to or less than about 10 seconds, equal to or less than about 8 seconds, equal to or less than about 7 seconds, equal to or less than about 6 seconds or equal to or less than about 5 seconds. In other embodiments, the disinfection system is capable of inactivating at least 99.99% of a pathogen traveling through the tunnel within any of the aforementioned travel times. In various embodiments, the pathogen is a virus, and the virus is Sars-Cov-2 or other coronavirus or an influenza virus or variants of any of the foregoing. The pathogen can also be a bacteria.

Another object of the invention is to provide a tunnel type letter and package conveyor disinfection system that can be integrated with current letter and package conveyor handling machines and is capable of inactivating 99.9% of a pathogen during the time it takes for the package or letter (object) to travel from an entry side of the tunnel to an exit side of the tunnel and that time is equal to or less than about 30 seconds, equal to or less than about 10 seconds, equal to or less than about 8 seconds, equal to or less than about 7 seconds, equal to or less than about 6 seconds, or equal to or less than about 5 seconds. In one embodiment, the pathogen is a virus, such as an influenza virus, or a coronavirus, including without limitation, SARS, MERS and Sars-Cov-2 or their respective variants. In another embodiment, the pathogen is a bacteria or a fungus. In another embodiment, the system is capable of inactivating at least 99.99% of a coronavirus or 99.9% of a coronavirus. In one embodiment, the coronavirus is Sars-Cov-2 or a variant (sometimes referred to as a mutation) thereof.

In one exemplary embodiment, a letter and package disinfection system forming a tunnel with at least twelve UVC emitting light bulbs is provided. The system has a roller assembly operated by a motor that causes the roller assembly to convey objects at a rate of between about 0.5 m/second and about 4.0 m/second from an entry end of the system to an exit end of the system, such that the travel time between the entry end of the system and the exit end of the system is equal to or less than about 30 seconds, equal to or less than about 10 seconds, equal to or less than about 8 seconds, equal to or less than about 7 seconds, equal to or less than about 6 seconds, or equal to or less than about 5 seconds. In one embodiment, the system has a roller assembly operated by a motor that causes the roller assembly to convey objects at a rate of about 2.0 m/second. In one embodiment, the system is capable of inactivating at least 99.9% of Sars-Cov-2 viruses (or variants) passing through the tunnel within the travel time inside the tunnel. In another embodiment, the system is capable of inactivating at least 99.99% of Sars-Cov-2 viruses (or variants) passing through the tunnel within the travel time inside the tunnel. In other embodiments, the travel time inside the tunnel is equal to or less than about 10 seconds, equal to or less than about 8 seconds, equal to or less than about 7 seconds, equal to or less than about 6 seconds or equal to or less than about 5 seconds, and the system is capable of inactivating at least 99.9% of Sars-Cov-2 viruses (or variants) passing through the tunnel within those travel times, or 99.99% of Sars-Cov-2 viruses (or variants) passing through the tunnel within those travel times. The system is capable of inactivating 99.9% or 99.99% of viruses, including influenza viruses and coronaviruses, including without limitations, SARS, MERS and Sars-Cov-2 and variants or mutations thereof within the above travel times through the tunnel. The pathogen being inactivated can also be a bacteria.

Other objects and advantages of the present invention will become apparent from the following descriptions, taken in connection with the accompanying drawings, wherein, by way of illustration and example, various embodiments of the present invention are disclosed.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION

Figure 1:
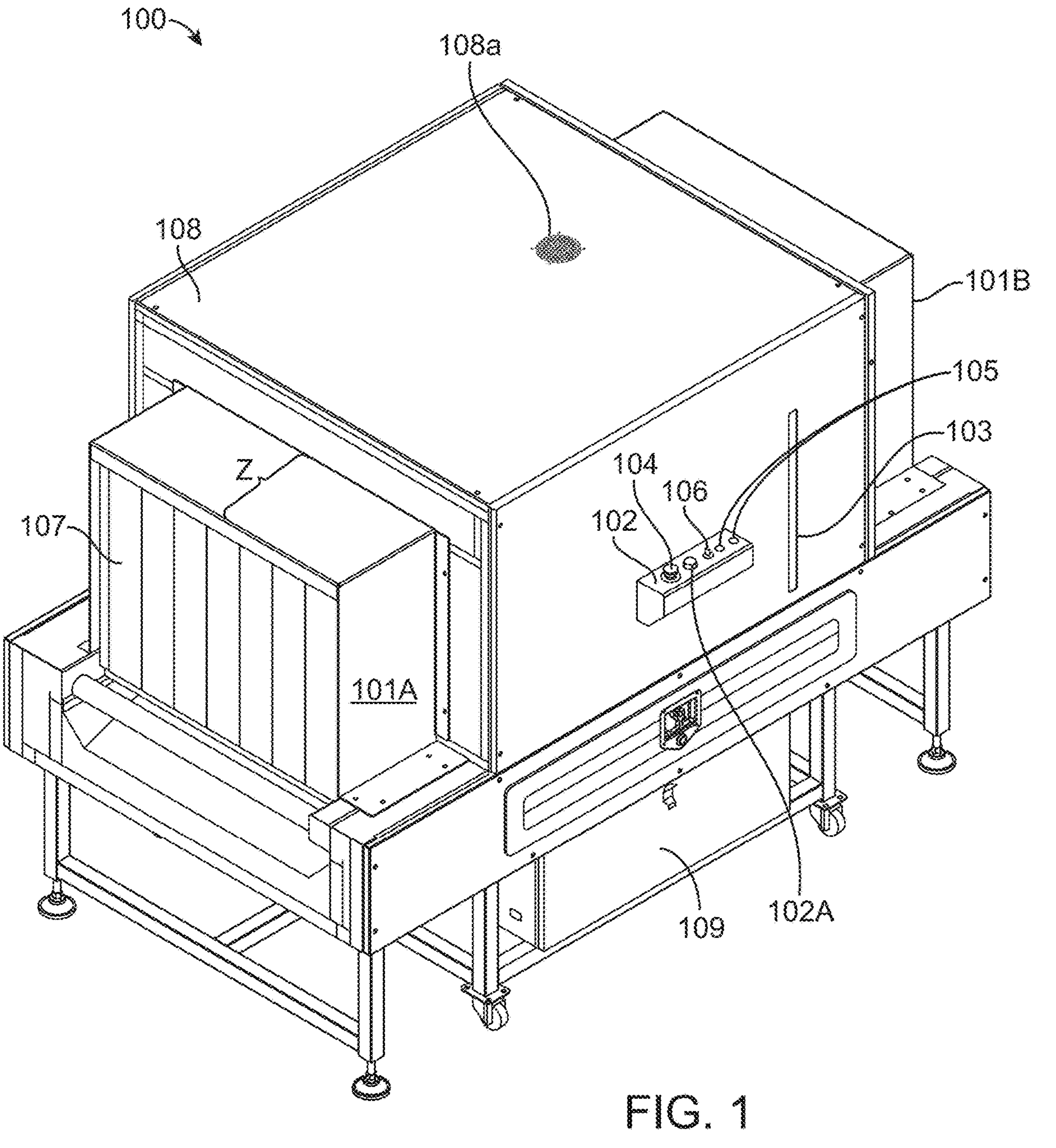
FIG. 1 is a side elevation view of a tunnel type baggage or cargo conveyor disinfection system in accordance with one embodiment.

Exemplary embodiments of the invention are shown in the accompanying Figures. In accordance with one embodiment, FIG. 1 shows a tunnel type letter, package, baggage or cargo conveyor disinfection system 100 (hereinafter the "tunnel-type system"). The tunnel-type system 100 is designed to disinfect objects that are conveyed through the tunnel 101 of the tunnel-type system 100 safely and effectively. The system uses UVC light bulbs disposed in an optimized 360° fashion within the tunnel 101. UVC light is known to inactivate pathogens by disrupting their DNA or RNA thus rendering them unable to propagate and grow. The optimal wavelength of light for disrupting DNA and RNA is between 250 and 260 nanometers. In order to be effective, the tunnel-type system 100 must inactivate at least 99.9% of the pathogens which are desired to be inactivated. For example, if the intent of the user is to inactivate Sars-Cov-2 or its variants, the tunnel-type system 100 must inactivate at least 99.9% of Sars-Cov-2 or its variants found on the surface of the objects that are conveyed through the tunnel 101 during the time in which they are in the tunnel 101. More preferably, the tunnel-type system 100 is even more effective (log 4 reduction versus log 3 reduction) when it inactivates 99.99% of Sars-Cov-2 or its variants found on the surface of the objects that are conveyed through the tunnel 101 during the time in which the objects are within the tunnel. This additional log reduction in virus is an important factor in reducing the transmission of pathogens like SARS-Cov-2, particularly in public spaces with large numbers of people, such as airports, sporting events, courthouses, jails and prisons, train stations, bus depots, shopping malls, and the like.

The tunnel-type system 100 is an assembly of various components. It includes a light blocking barrier 108 on the top side and two opposing left and right sides of the tunnel, thus preventing UVC light from exiting the tunnel. UVC light can be harmful to human skin and eyes. The barrier 108 prohibits light from escaping the tunnel, thus preventing any harm from UVC light to humans or animals that may be near the tunnel-type system 100. Each of the opposing left and right sides of the barrier 108 has a vertical slit 103 covered by plexi-glass or other transparent UVC blocking material. The slits 103 form windows into the tunnel 101 allowing the user to confirm that all of the UVC light bulbs inside the tunnel are operational. The tunnel-type system 100 has a command center 102 with a master on/off key 102A, an emergency stop button 104, on and off buttons 105, and an ozone sensor 106. The command center 102 is wired to a microprocessor control system located in an electronics housing 109. The electronics housing 109 contains all of the electronics needed to operate the system, a power cord or internal battery, a microprocessor, electromechanical relays, circuit breakers, switches, sensors and an electric motor driver. An electric motor (not shown) connected to the rollers 141 with a drive chain or belt drives the rollers 141.

The tunnel-type system 100 includes include entry and exit shields 101A and 101B to prevent UVC light from exiting the system 100 from entry and exit ends of the tunnel 101. The entry and exit shields 101A and 101B can each contain curtains 107 attached to them. Curtains 107 are not transparent or are made of transparent but UVC blocking material and can be attached to the top of the entry and exit shields 101A and 101B as shown in FIG. 1. Curtains 107 prevent UVC light from exiting the tunnel 101. Importantly, the entry shields 101A and 101B, do not contain any UV lights inside. In FIG. 1, the entry and exit shields 101A and 101B are shown as separate components from the cage 150 and connected to the cage 150 and base roller assembly 140 with bolts or screws. However, in another embodiment not shown, the entry and exit shields 101A and 101B can be formed as one continuous structure with the cage 150 and be an extension of the cage 150 on both the entry and exit ends of the system 101. One of the reasons why the entry and exit shields 101A and 101B are important is that they form a non-irradiated region or distance within the tunnel 101 before the irradiation region begins. This is important because curtains 107 swing inward as objects pass through them into the entry shield 101A, and any UVC light hitting the back of the curtains 107 that rest atop the objects passing through the tunnel 101 would be blocked by the curtains 107. Thus, the curtains 107 are offset from the region of the tunnel 101 where the UVC lights begin by a distance Z which constitutes the length of the entry shield 101, whether or not the entry shield 101A is a separate component from the cage 150 as shown in FIG. 1 or is formed integrally with the cage 150. Distance Z is approximately one half the height of the curtains 107. A second set of curtains (not shown) can also be attached to the entry and exit sides of the tunnel frame 150 (shown in FIG. 2). Thus, there can be two sets of curtains on both the entry side of the tunnel and the exit side of the tunnel providing two sets of containment barriers for the UVC light inside the tunnel 101.

Figure 2:
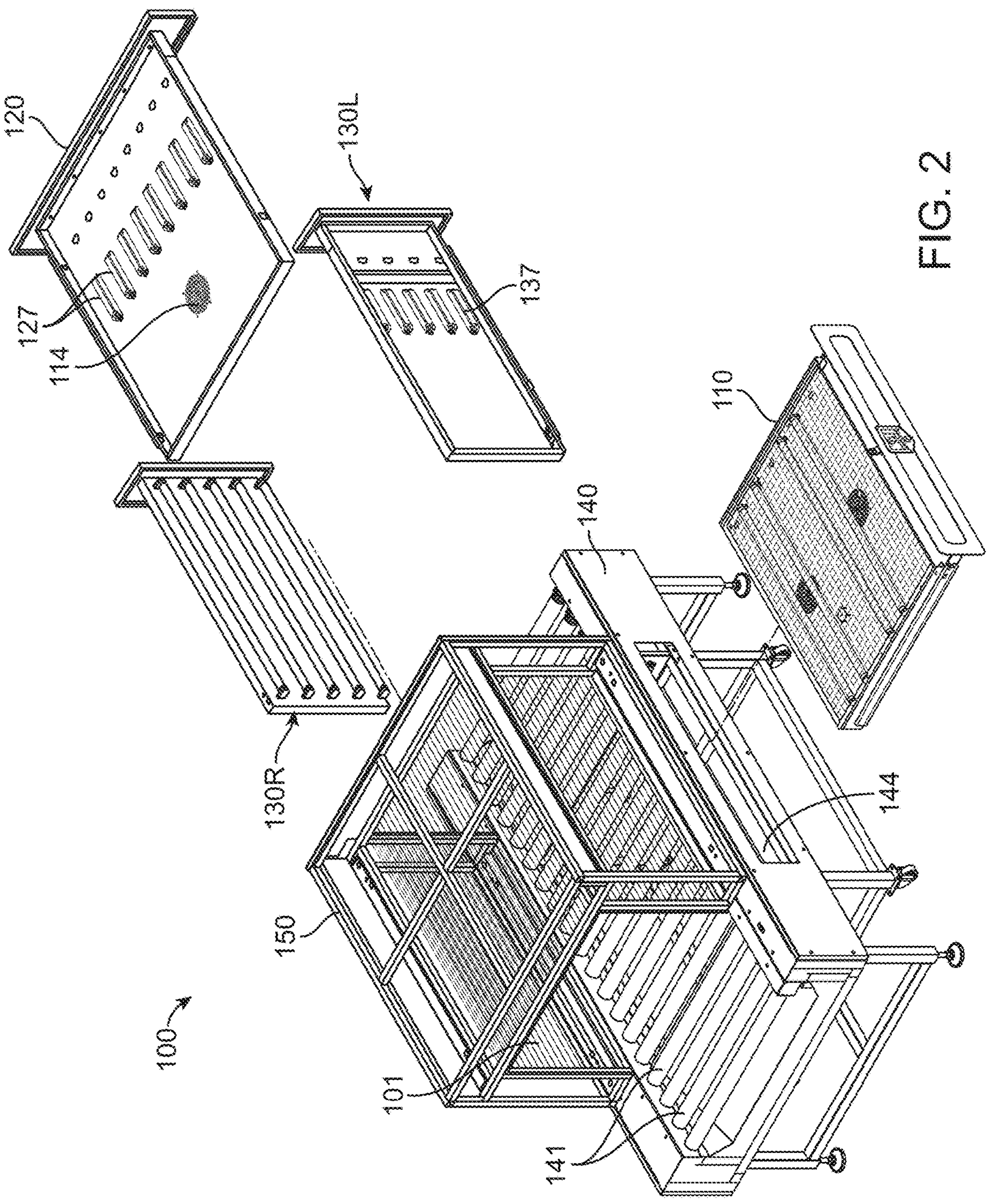
FIG. 2 is an exploded view of the tunnel type baggage or cargo conveyor disinfection system of FIG. 1.

FIG. 2 provides an exploded view of the tunnel-type system 100 excluding the entry and exit shields 101A and 101B. The tunnel-type system 100 includes a base 140, a tunnel frame 150, a bottom drawer UVC light bulb assembly 110, a sliding roof UVC light bulb assembly 120, a left sliding wall UVC light bulb assembly 130L, and a right sliding wall UVC light bulb assembly 130R. Base 140 contains the electronics housing 109 and a series of rollers 141. The electronics housing 109 includes a speed adjustable motor drive unit that operates a motor that drives the rollers 141, which are connected to one another with a drive chain or belt.

For a tunnel-type system 100 that is used to disinfect baggage and cargo, the motor drive unit can be adjusted to operate the motor to drive the rollers 141 to convey objects through the tunnel 101 at speeds of between about 0.10 m/second and about 0.50 m/second. In one exemplary embodiment, the motor drive unit operates the motor to drive the rollers 141 to convey objects through the tunnel 101 at speeds of about 0.20 m/second.

For a tunnel-type system 100 that is used to disinfect letters, packages and parcels, the motor drive unit can be adjusted to operate the motor to driver the rollers 141 to convey objects through the tunnel 101 at speeds of between about 0.50 m/second and about 4.0 m/second.

Figure 9:
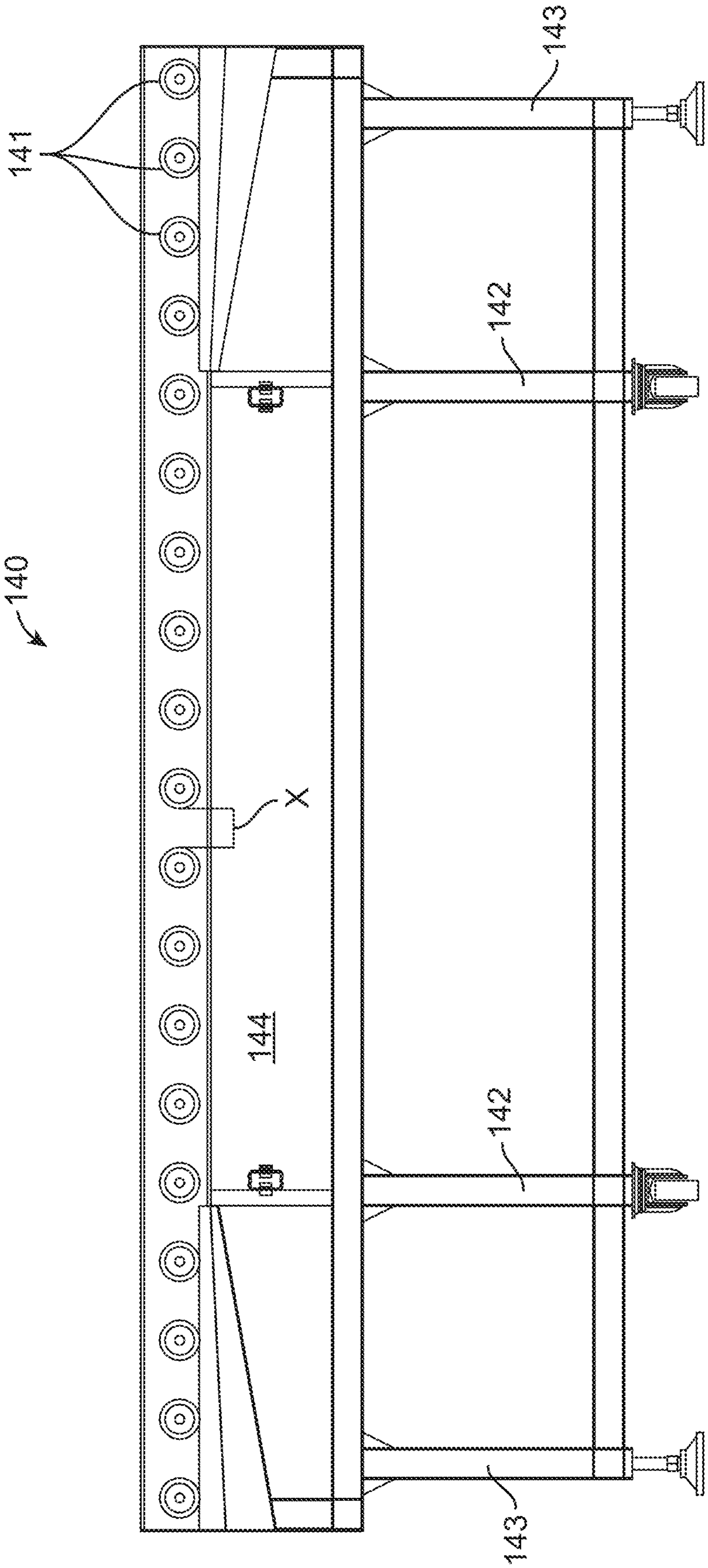
FIG. 9 is a side view of the base roller assembly of the tunnel type baggage or cargo conveyor disinfection system of FIG. 1.

As best shown in FIG. 9, base 140 has four rolling legs 142 that allow the tunnel-type system 100 to be rolled around from one place to another with ease. Rolling legs 142 have wheels attached to their bottom. The wheels can have locks on them to prevent the base 140 from rolling around when the locks are engaged. Base 140 can have another set of four legs 143 with height adjustable posts to raise or lower the tunnel-type system 100. Rollers 141 are set at a predetermined distance X from one another. In one embodiment, distance X is between about 20 mm and about 100 mm. In another embodiment, distance X is between about 30 mm and about 90 mm. In another embodiment, distance X is between about 40 mm and about 80 mm. In another embodiment, distance X is between about 40 mm and about 70 mm. In another embodiment, distance X is between about 40 mm and about 60 mm. In another embodiment, distance X is about 50 mm. In another embodiment, distance X is about 60 mm. In another embodiment, distance X is about 70 mm. Distance X is important to the proper functioning of the tunnel-type system 100, because UVC light emitted from the bottom drawer UVC light bulb assembly 110 to the bottom side of an object resting on the rollers 141 is blocked by the rollers 141. Thus, the rollers 141 must be spaced far enough apart to allow enough light to reach the bottom side of the object traveling through the tunnel 101 across the rollers 141 in order to inactivate any pathogens located on the bottom side of the object. However, the rollers cannot be spaced so far apart that they allow the object being disinfected to fall through the gaps in the rollers 141.

Base 140 has an opening 144 to receive bottom drawer UVC light bulb assembly 110. UVC bottom drawer light bulb assembly 110 is slideably engaged with base 140 in opening 144 with side mount drawer slides or any other type of drawer slides and tracks commonly used for cabinetry and drawers.

Figure 4:
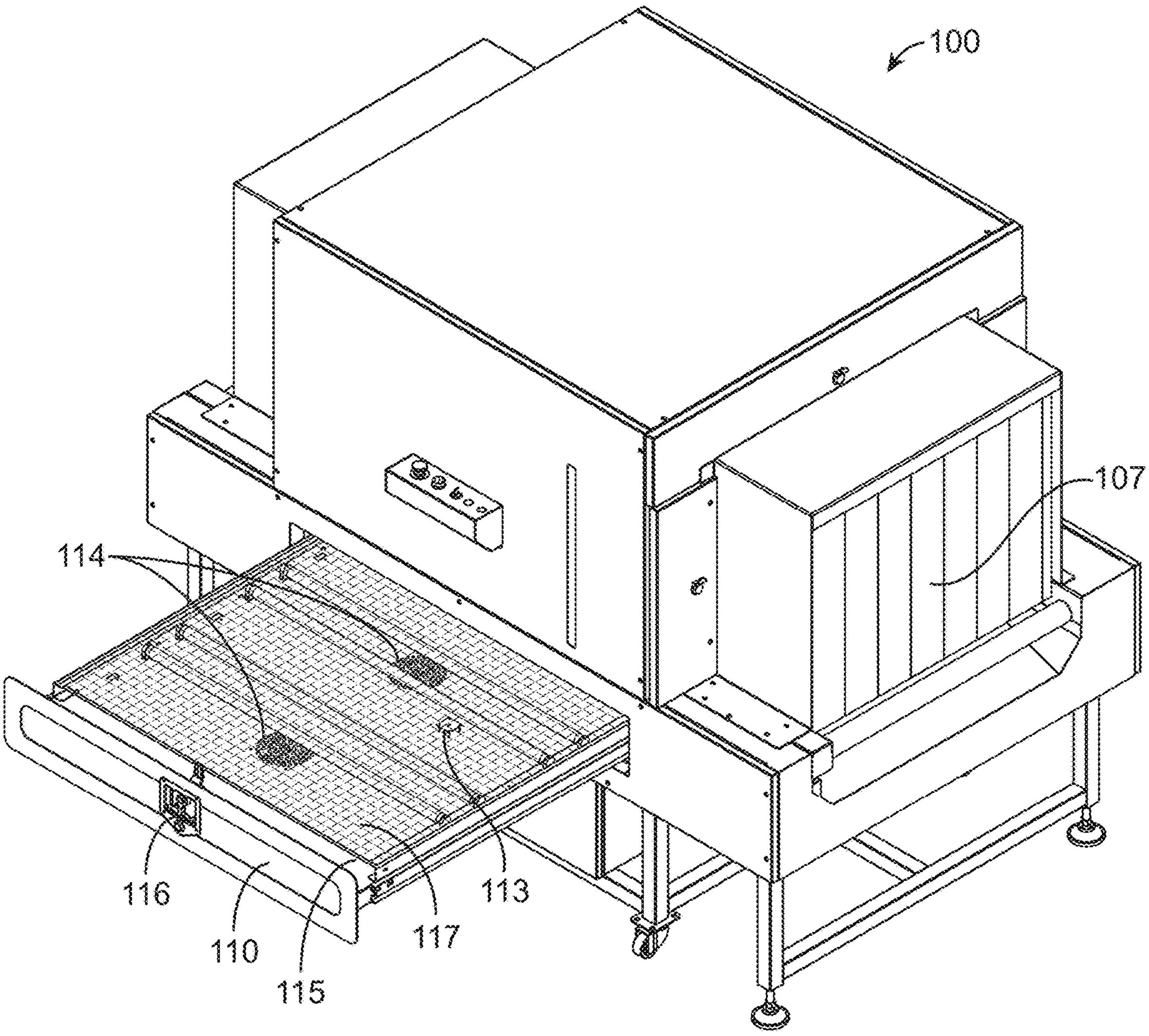
FIG. 4 is another side elevation view from another angle of the tunnel type baggage or cargo conveyor disinfection system of FIG. 1.

As shown more clearly in FIG. 4, bottom drawer light bulb assembly 110 has a wire safety mesh 117 resting atop the drawer. Wire safety mesh 117 is removable. If any small objects fall through the gaps between the rollers 141, those small objects are caught by wire safety mesh 117, which acts as a protective barrier for the UVC light bulbs 110A inside bottom drawer light bulb assembly 110. Those fallen objects can be retrieved by sliding bottom drawer UVC light bulb assembly 110 open and retrieving the object from atop the wire safety mesh 117. UVC bottom drawer light bulb assembly 110 also has a latch and handle 116. The latch and handle 116 locks drawer 110 and can be used to pull drawer 110 open.

Figure 5:
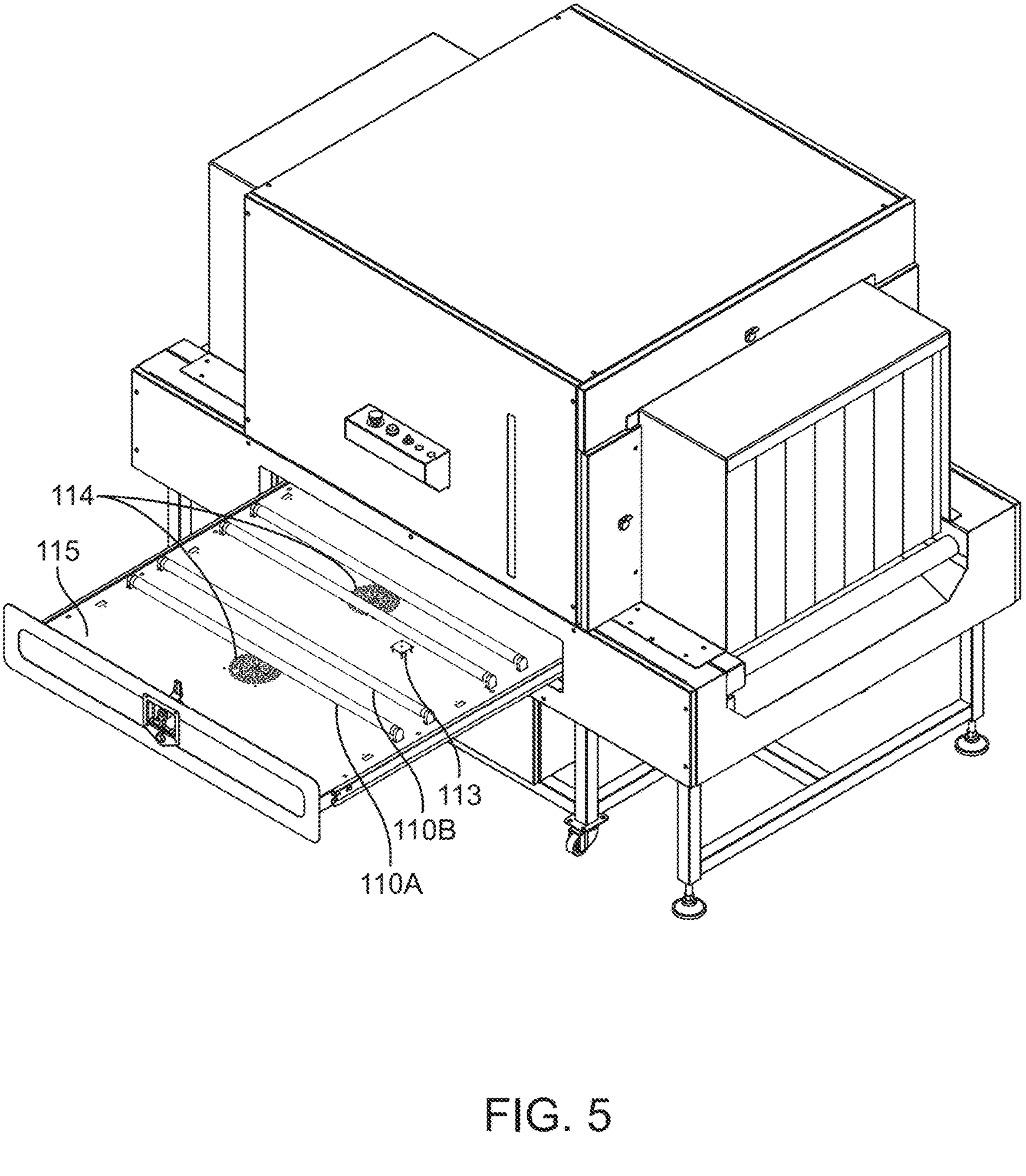
FIG. 5 is another side elevation view of the tunnel type baggage or cargo conveyor disinfection system of FIG. 1.

FIG. 5 shows drawer 110 with the wire safety mesh 117 removed. The base 115 of drawer 110 has a reflective material such as aluminum that reflects UVC light. Attached to the base 115 is a UVC light sensor 113 that is wired to the microprocessor contained in the electronics housing 109. Sensor 113 sends a signal to the microprocessor if it is not receiving sufficient UVC light, thus indicating that at least one of the light bulbs is not operational. The microprocessor initiates an output signal to trigger the malfunction alarm 102A to signal an inoperative or weak UVC lamp within the tunnel-type system 100. Running parallel with the tunnel-type system 110 are a series of UVC light bulbs 110A (as shown in FIG. 5). UVC light bulbs 110A irradiate the bottom side of objects that travel through the tunnel 101. Sufficient UVC light must reach the bottom side of the objects in order to inactivate an effective amount of pathogens (at least 99.9% and preferably 99.99%) within the time of travel of the objects through the tunnel 101. In one embodiment, it has been determined that four 30 W Osram® UVC light bulbs are sufficient to inactivate pathogens, such as Sars-Cov-2 when the travel time of an object within the tunnel is about 5 seconds. However, the bottom drawer 110 can have between one and eight sets of UVC light bulb sockets 110B to accommodate up to eight UVC light bulbs 110A. In one embodiment, four UVC light bulbs 110A are connected to four sets of sockets 110B respectively. In one embodiment, the light bulbs 110A are each 30 W Osram® UVC light bulbs emitting a dominant wavelength of 254 nm. In another embodiment, they are 30 W Phillips UVC light bulbs emitting a dominant wavelength of 254 nm. Each set of sockets 110B is wired to a UVC light bulb ballast, which is wired to a relay in the electronics housing 109, which is wired to the microprocessor. The bottom drawer 110 also includes at least one fan 114 (two fans are shown in the Figures) in order to cool the tunnel type system 100. The fans 114 can also be hard wired to the microprocessor or to the on and off buttons 105 through the electromechanical relay. The fans 114 can draw the warm air within the tunnel-type system 100 and expel it out through exit ports on the bottom side of the bottom drawer 110. A fan 114 can also be located on the sliding roof UVC light bulb assembly 120 to serve the same purpose as the fans 114 on the bottom drawer 110. The fan 114 on the sliding roof UVC light bulb assembly 120 can expel air through outlet holes or exit ports 108A on the top side of the light blocking barrier 108. An interlock switch (not shown) can be attached to the drawer 110 or to the base and when the drawer is pulled out, it can trip the interlock switch to cut all power to the UVC light bulbs and the electric motor driving the rollers 141.

UVC light can generate ozone, and excessive amounts of ozone can be harmful to the environment or hazardous to human health. Whether or not ozone is generated within safe limits or exceeds safe limits depends on how much UVC light is emitted by a system. To reduce ozone emissions to within acceptable safety limits, one can either limit the amount of UVC light emitted or reduce the emission of ozone into the atmosphere that is generated by the UVC light. In one embodiment, one or more ozone filters are incorporated into the tunnel-type system 100. They can be located in various parts or locations within the tunnel-type system 100. In one embodiment, an ozone filter can be in fluid communication with the fan(s) 114 so that the air that is drawn out of the tunnel-type system by the fan(s) 114 is filtered through an ozone filter that filters out the ozone before the air is expelled into the surrounding environment.

Figure 3:
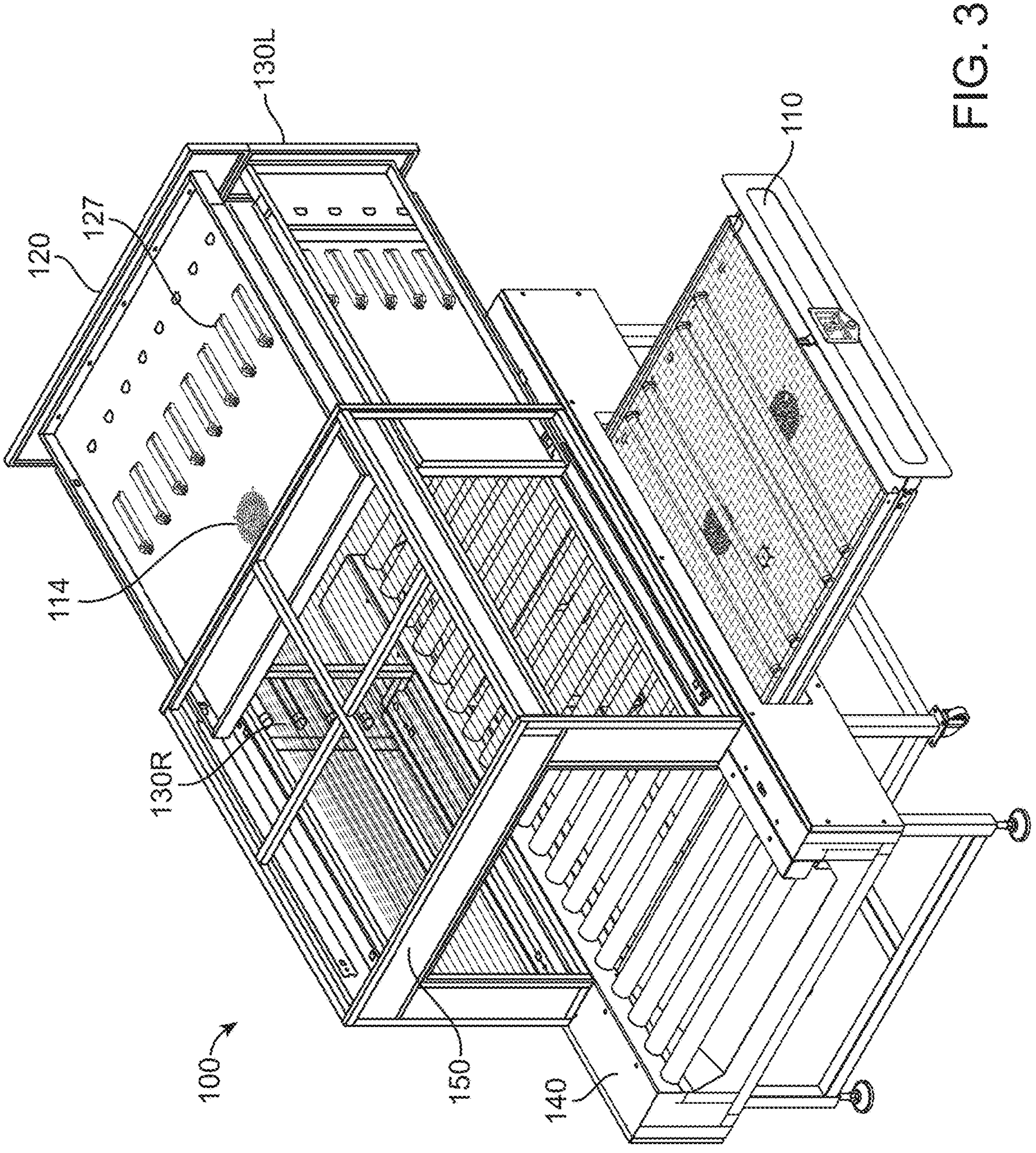
FIG. 3 is another side elevation view of the tunnel type baggage or cargo conveyor disinfection system of FIG. 1.
Figure 8:
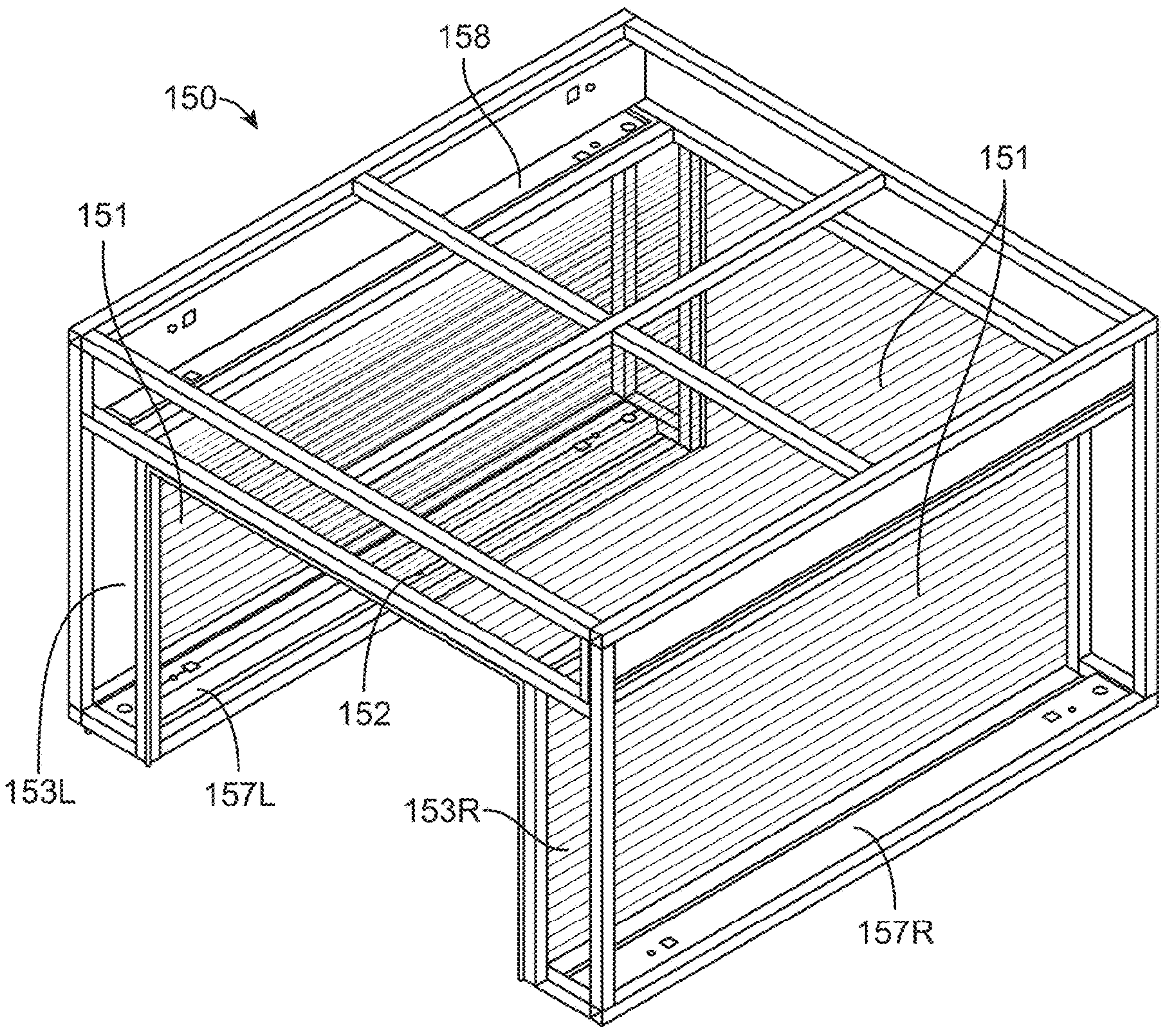
FIG. 8 is a side elevation view of the frame of the tunnel type baggage or cargo conveyor disinfection system of FIG. 1.

The tunnel-type system 100 also includes tunnel frame 150 as shown in FIG. 8. Tunnel frame 150 is secured to base 140 as shown in FIGS. 2 and 3. Tunnel frame 150 can be secured to base 140 with bolts or by welding it to the base. Protective wires or a protective wire mesh 151 extends across the inner windows of each of the top, left and right sides of the frame 150. The outer windows of the top, left and right sides of the frame 150 are exposed as shown in FIG. 8, except for a beam on the top outer window that provides structural integrity to the tunnel frame 150. Wire mesh 151 forms a protective barrier between the UVC light bulbs of the tunnel-type system 100 and the objects that are traveling through the tunnel 101 as will be explained in more detail below. Tunnel frame 150 has a top opening 152 that receives sliding roof UVC light bulb assembly 120. There are tracks 158 on the left and right side of the tunnel frame 150 top opening 152 that mate with drawer slides attached to the left and right side of sliding roof UVC light bulb assembly 120. Sliding roof UVC light bulb assembly 120 can slide in and out of the top opening 152 of the tunnel frame 150 like an upside-down drawer as shown in FIG. 3. Tunnel frame 150 has a left opening 153L that receives left sliding wall UVC light bulb assembly 130L. There is a track 157L on the left bottom (or alternatively top) surface of the tunnel frame 150 that mates with a drawer slide on the bottom (or alternatively top) of left sliding wall UVC light bulb assembly 130L. Left sliding wall UVC light bulb assembly 130L can slide in and out of left opening 153L of the tunnel frame 150 like a sideways drawer. Tunnel frame 150 has a right opening 153R that receives right sliding wall UVC light bulb assembly 130R. There is a track 157R on the right bottom (or alternatively top) surface of the tunnel frame 150 that mates with a drawer slide on the bottom (or alternatively top) of the right sliding wall UVC light bulb assembly 130R. Right sliding wall UVC light bulb assembly 130R can slide in and out of right opening 153R of the tunnel frame 150 like a sideways drawer.

FIG. 3 shows all of the drawers 110, 120, 130L (and 130R not visible) all pulled out from the tunnel frame 150 and the base 140. This unique sliding drawer design makes it very easy to change the UVC light bulbs of the tunnel-type system 100. One need only slide open the drawer that has the broken or inoperative light bulb, remove the light bulb from its socket, replace it with a new light bulb, and slide the drawer back into the closed position.

Figure 6:
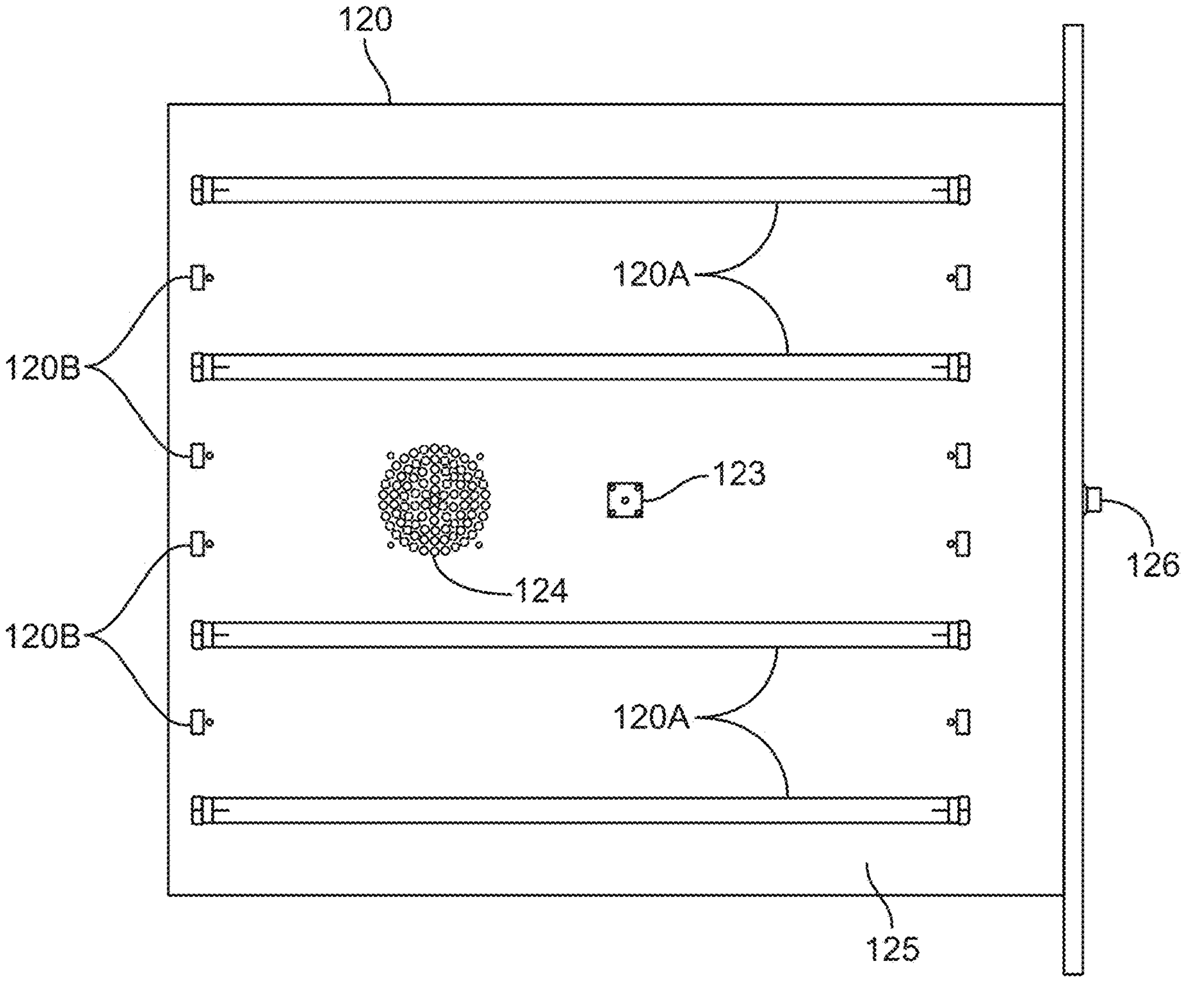
FIG. 6 is a bottom view of the top drawer light bulb assembly of the tunnel type baggage or cargo conveyor disinfection system of FIG. 1.

Referring now to FIGS. 3 and 6, sliding roof UVC light bulb assembly 120 is described in more detail. FIG. 6 shows the bottom side of sliding roof UVC light bulb assembly 120 (sometimes referred to as the top drawer). The bottom side has a reflective surface 125 made from any reflective material, such as aluminum, which can efficiently reflect UV light. Attached to the bottom side 125 of the assembly 120 is a UVC light sensor 123 that is wired to the microprocessor contained in the electronics housing 109. Sensor 123 sends a signal to the microprocessor if it is not receiving sufficient UVC light, thus indicating that at least one of the light bulbs is not operational. The microprocessor initiates an output signal to trigger the malfunction alarm 102A to signal an inoperative or weak UVC lamp within the tunnel-type system 100. The bottom side 125 also has air openings 124 matched to a fan on the top side of the drawer, which draws hot air out from inside the tunnel through the openings 124 and out of the system 100. Running parallel with the tunnel-type system 110 are a series of UVC light bulbs 120A (as shown in FIG. 6). UVC light bulbs 120A irradiate the top side of objects that travel through the tunnel 101. Sufficient UVC light must reach the top side of the objects in order to inactivate an effective amount of pathogens (at least 99.9% and preferably 99.99%) within the time of travel of the objects through the tunnel 101. In one embodiment, it has been determined that four 30 W Osram® UVC light bulbs are sufficient to inactivate pathogens, such as Sars-Cov-2 when the travel time of an object within the tunnel is about 5 seconds. However, assembly 120 can have between one and eight sets of UVC light bulb sockets 120B to accommodate up to eight UVC light bulbs 120A. In one embodiment, four UVC light bulbs 120A are connected to four sets of sockets 120B respectively. In one embodiment, the light bulbs 120A are each 30 W Osram® UVC light bulbs emitting a dominant wavelength of 254 nm. In another embodiment, they are 30 W Phillips® UVC light bulbs emitting a dominant wavelength of 254 nm. Each set of sockets 120B is wired to a UVC light bulb ballast 127, which is wired to a relay in the electronics housing 109, which is wired to the microprocessor. An interlock switch (not shown) can be attached to the assembly 120 or to the tunnel frame 150 and when the assembly 120 is pulled out, it can trip the interlock switch to cut all power to the UVC light bulbs and the electric motor driving the rollers.

Figure 7:
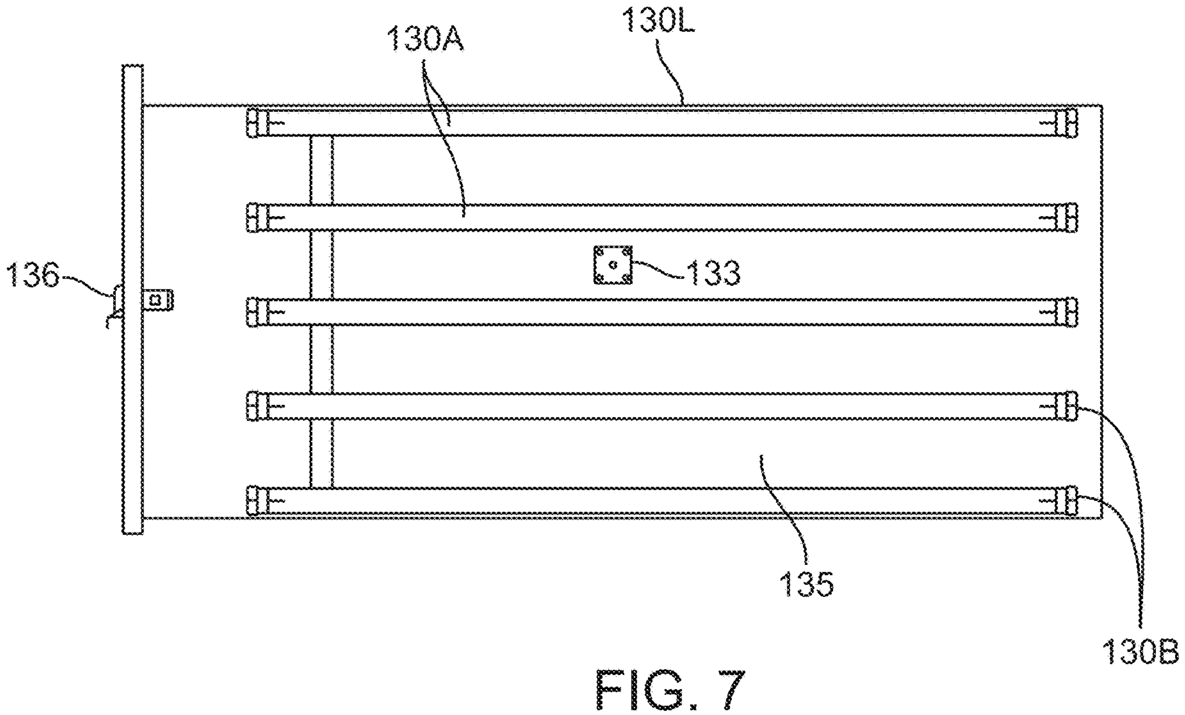
FIG. 7 is a direct view of the internal side of the left drawer light bulb assembly of the tunnel type baggage or cargo conveyor disinfection system of FIG. 1.

Referring now to FIGS. 2 and 7, left sliding wall UVC light bulb assembly 130L is described in more detail. All of the detail set forth herein for sliding wall UVC light bulb assembly 130L is the same with respect to right sliding wall UVC light bulb assembly 130R. FIG. 7 shows the tunnel facing side of left sliding wall UVC light bulb assembly 130L (sometimes referred to as the left drawer). The tunnel facing side has a reflective surface 135 made from any reflective material, such as aluminum, which can efficiently reflect UV light. Attached to the tunnel facing side 135 of the assembly 130L is a UVC light sensor 133 that is wired to the microprocessor contained in the electronics housing 109. Sensor 133 sends a signal to the microprocessor if it is not receiving sufficient UVC light, thus indicating that at least one of the light bulbs is not operational. The microprocessor initiates an output signal to trigger the malfunction alarm 102A to signal an inoperative or weak UVC lamp within the tunnel-type system 100. Running parallel with the tunnel of the tunnel-type system 110 are a series of UVC light bulbs 130A (as shown in FIG. 7). UVC light bulbs 130A irradiate the side and top of objects that travel through the tunnel 101. Sufficient UVC light must reach the top and side of the objects in order to inactivate an effective amount of pathogens (at least 99.9%) within the time of travel of the objects through the tunnel 101. In one embodiment, it has been determined that four 30 W Osram® UVC light bulbs are sufficient to inactivate pathogens, such as Sars-Cov-2 when the travel time of an object within the tunnel 101 is about 5 seconds. However, assembly 130L can have between one and five sets of UVC light bulb sockets 130B to accommodate up to five UVC light bulbs 130A. In one embodiment, five UVC light bulbs 130A are connected to five sets of sockets 130B respectively. In one embodiment, the light bulbs 130A are each 30 W Osram® UVC light bulbs emitting a dominant wavelength of 254 nm. In another embodiment, they are 30 W Phillips® UVC light bulbs emitting a dominant wavelength of 254 nm. Each set of sockets 130B is wired to a UVC light bulb ballast 137, which is wired to a relay in the electronics housing 109, which is wired to the microprocessor. An interlock switch 136 can be attached to the assembly 130L or to the tunnel frame 150 and when the assembly 130L is pulled out, it can trip the interlock switch 136 to cut all power to the UVC light bulbs and the electric motor driving the rollers.

In one embodiment, the tunnel 101 is about 75 cm in height, about 55 cm in width, and about 150 cm in length. In this embodiment, the length of the tunnel 101 that contains the irradiated region can be about 90-100 cm in length with non-irradiated entry and exit regions 101A and 101B each having a length Z of about 25-30 cm as shown in FIG. 1. With respect to the aforementioned tunnel 101 dimensions of the tunnel-type system 100, the applicants have determined that sufficient inactivation of pathogens can be achieved with no fewer than fourteen 30 W UVC light bulbs emitting a dominant wavelength of 254 nm, preferably with five light bulbs 120A in the top drawer 120, three light bulbs 110A in the bottom drawer 110, and three light bulbs 130A on each of the left and right drawers 130L and 130R. In another embodiment, the tunnel-type system 100 contains no fewer than eighteen 30 W UVC light bulbs emitting a dominant wavelength of 254 nm, preferably with four light bulbs 120A in the top drawer 120, four lights bulbs 110A in the bottom drawer 110, and five light bulbs 130A on each of the left and right drawers 130L and 130R. In another embodiment, the tunnel-type system 100 contains eighteen 30 W UVC light bulbs emitting a dominant wavelength of 254 nm, preferably with five light bulbs 120A in the top drawer 120, three light bulbs 110A in the bottom drawer 110, and five light bulbs 130A on each of the left and right drawers 130L and 130R. In another embodiment, the tunnel-type system 100 contains no fewer than twenty 30 W UVC light bulbs emitting a dominant wavelength of 254 nm, preferably with six light bulbs 120A in the top drawer 120, four lights bulbs 110A in the bottom drawer 110, and five light bulbs 130A on each of the left and right drawers 130L and 130R. In another embodiment, the tunnel-type system 100 contains no fewer than twenty 30 W UVC light bulbs emitting a dominant wavelength of 254 nm, preferably with five light bulbs 120A in the top drawer 120, five lights bulbs 110A in the bottom drawer 110, and five light bulbs 130A on each of the left and right drawers 130L and 130R. In another embodiment, the tunnel-type system 100 contains no fewer than twenty-two 30 W UVC light bulbs emitting a dominant wavelength of 254 nm, preferably with seven light bulbs 120A in the top drawer 120, five lights bulbs 110A in the bottom drawer 110, and five light bulbs 130A on each of the left and right drawers 130L and 130R. In another embodiment, the tunnel-type system 100 contains no fewer than twenty-four 30 W UVC light bulbs emitting a dominant wavelength of 254 nm, preferably with eight light bulbs 120A in the top drawer 120, six lights bulbs 110A in the bottom drawer 110, and five light bulbs 130A on each of the left and right drawers 130L and 130R. In another embodiment, the tunnel-type system 100 contains no fewer than twenty-six 30 W UVC light bulbs emitting a dominant wavelength of 254 nm, preferably with eight light bulbs 120A in the top drawer 120, eight lights bulbs 110A in the bottom drawer 110, and five light bulbs 130A on each of the left and right drawers 130L and 130R. In each of the above embodiments, the light bulbs are about 90 cm in length.

In another embodiment, the tunnel 101 is about 60 cm in height, about 40 cm in width, and about 150 cm in length, and the number and arrangement of light bulbs is as set forth above. In another embodiment, the tunnel 101 is about 60 cm in height, about 40 cm in width, and about 100 cm in length. In this shorter embodiment, it has been determined that sufficient inactivation of pathogen can be achieved with no fewer than eighteen 25 W UVC light bulbs emitting a dominant wavelength of 254 nm with each light bulb being about 44 cm in length. In one embodiment, the tunnel 101 is about 60 cm in height, about 40 cm in width, and about 100 cm in length with twenty 25 W UVC light bulbs emitting a dominant wavelength of 254 nm, preferably with six light bulbs 120A in the top drawer 120, four light bulbs 110A in the bottom drawer 110, and five light bulbs 130A on each of the left and right drawers 130L and 130R, with each light bulb being about 44 cm in length. In another embodiment, the tunnel 101 is about 60 cm in height, about 40 cm in width, and about 100 cm in length with twenty-two 25 W UVC light bulbs emitting a dominant wavelength of 254 nm, preferably with seven light bulbs 120A in the top drawer 120, five light bulbs 110A in the bottom drawer, and five light bulbs 130A on each of the left and right drawers 130L and 130R, with each light bulb being about 44 cm in length. In another embodiment, the tunnel 101 is about 60 cm in height, about 40 cm in width, and about 100 cm in length with twenty-four 25 W UVC light bulbs emitting a dominant wavelength of 254 nm, preferably with eight light bulbs 120A in the top drawer 120, six light bulbs 110A in the bottom drawer, and five light bulbs 130A on each of the left and right drawers 130L and 130R, with each light bulb being about 44 cm in length. In another embodiment, the tunnel 101 is about 60 cm in height, about 40 cm in width, and about 100 cm in length with twenty-six 25 W UVC light bulbs emitting a dominant wavelength of 254 nm, preferably with eight light bulbs 120A in the top drawer 120, eight light bulbs 110A in the bottom drawer, and five light bulbs 130A on each of the left and right drawers 130L and 130R, with each light bulb being about 44 cm in length.

In another embodiment, the tunnel 101 is about 100 cm in height, about 100 cm in width, and about 150 cm in length. In this larger size, it has been determined that sufficient inactivation of pathogen can be achieved with no fewer than twenty 30 W UVC light bulbs emitting a dominant wavelength of 254 nm with each light bulb being about 90 cm in length. In one embodiment, the tunnel 101 is about 100 cm in height, about 100 cm in width, and about 150 cm in length with twenty 30 W UVC light bulbs emitting a dominant wavelength of 254 nm, preferably with six light bulbs 120A in the top drawer 120, four light bulbs 110A in the bottom drawer 110, and five light bulbs 130A on each of the left and right drawers 130L and 130R, with each light bulb being about 90 cm in length. In another embodiment, the tunnel 101 is about 100 cm in height, about 100 cm in width, and about 150 cm in length with twenty-two 30 W UVC light bulbs emitting a dominant wavelength of 254 nm, preferably with seven light bulbs 120A in the top drawer 120, five light bulbs 110A in the bottom drawer, and five light bulbs 130A on each of the left and right drawers 130L and 130R, with each light bulb being about 90 cm in length. In yet another embodiment, the tunnel 101 is about 100 cm in height, about 100 cm in width, and about 150 cm in length with twenty-four 30 W UVC light bulbs emitting a dominant wavelength of 254 nm, preferably with eight light bulbs 120A in the top drawer 120, six light bulbs 110A in the bottom drawer, and five light bulbs 130A on each of the left and right drawers 130L and 130R, with each light bulb being 90 cm in length. In yet another embodiment, the tunnel 101 is about 100 cm in height, about 100 cm in width, and about 150 cm in length with twenty-six 30 W UVC light bulbs emitting a dominant wavelength of 254 nm, preferably with eight light bulbs 120A in the top drawer 120, eight light bulbs 110A in the bottom drawer, and five light bulbs 130A on each of the left and right drawers 130L and 130R, with each light bulb being 90 cm in length.

With respect to any of the above embodiments of tunnel sizes, the length of the tunnel can be extended by about 50 cm and a second series of UVC light bulbs can be added in succession either in front of or behind the UVC light bulbs 110A, 120A, and 130A thus extending the region of irradiation by about 45-50 cm. To accomplish this, additional 25 W or 30 W UVC light bulbs having a length of about 44 cm is added to each of the drawers. In this case, each of the drawers is lengthened by about 45-50 cm. Drawer 110 thus contains up to an additional eight 44 cm UVC light bulbs, drawer 120 contains up to an additional eight 44 cm UVC light bulbs, and drawers 130L and 130R each contain up to an additional five 44 cm UVC light bulbs. This allows for a longer period of irradiation as the irradiated objects must travel through a tunnel that is about 50 cm longer having a region of irradiation that is about 45-50 cm longer.

With respect to any of the embodiments of tunnel sizes, the length of the tunnel can be extended by about 100 cm and a second series of UVC light bulbs can be added in succession either in front of or behind the UVC light bulbs 110A, 120A, and 130A thus extending the region of irradiation by about 90-100 cm. To accomplish this, additional 30 W UVC light bulbs having a length of about 90 cm is added to each of the drawers. In this case, each of the drawers is lengthened by about 90-100 cm. Drawer 110 thus contains up to an additional eight 90 cm UVC light bulbs, drawer 120 contains up to an additional eight 90 cm UVC light bulbs, and drawers 130L and 130R each contain up to an additional eight 90 cm UVC light bulbs. This allows for a longer period of irradiation as the irradiated objects must travel through a tunnel that is about 100 cm longer having a region of irradiation that is about 90-100 cm longer.

The light bulbs described herein can be Osram®, Phillips® or other brand that makes UVC light bulbs emitting a dominant wavelength of about 254 nm and having a 25 W or 30 W nominal wattage.

The tunnel-type system 100 of the present invention is capable of inactivating 99.99% of Sars-Cov-2 (log 4 reduction) and 99.9% of bacteria (log 3 reduction) within 5 seconds as a result of the optimal combination of the following factors and conditions: light bulb strength; wavelength of light emitted; optimal placement of light bulbs within the tunnel; distance of light bulbs from the objects being conveyed; and the length of time that the objects are irradiated with UVC light as a function of the speed of the conveyor that carries the objects through the tunnel and the length of the tunnel.

Example 1

Conveyor Type UVC Baggage and Cargo Disinfection System

The experiment was performed with an XRC CLEAN-BLUE™ 75-55 CONVEYOR TYPE UVC BAGGAGE CLEANING SYSTEM (the "XRC System"). The system contains a tunnel size of about 75 cm in width, about 55 cm in height, and about 150 cm length in total with an irradiation region of about 95 cm in length. The system contains 18 Osram® nominal 30 W UVC lamps of 90 cm in length emitting a dominant wavelength of 254 nm arranged in the following manner: four light bulbs in the top drawer, four light bulbs in the bottom drawer, and five light bulbs on each of the left and right drawers. The rollers of the XRC system operate at a speed that conveys objects through the tunnel at about 0.20 m/second. The total irradiation time in the tunnel of the XRC System is therefore about 5 seconds.

The bacteria being tested were *S. aureus* (ATCC:6538) and *E. hirae* (ATCC:10541). The exposure time to UVC light was five seconds. The test environment was 23±2° C. The bacteria Incubation was 37° C.±1° C., 5% CO2.

Test Method:

Bacteria suspensions of *S. aureus* and *E. hirae* were prepared using diluent and microorganism N number was determined by UV spectrophotometer. Two control petri dishes and three test petri dishes for each of the two types of bacteria were prepared. The XRC System was operated for 5 minutes before testing and the UVC lamps were warmed up. Two control petri dishes containing *S. aureus* bacterial samples were placed on the top of a platform having a height of about 20 cm (the platform being roughly the size and dimensions of a suitcase) and the test was carried out within the tunnel of the XRC System without the UVC lamps being turned. Then three test petri dishes containing *S. aureus* bacterial samples were placed on the top of the same platform and the test was carried out within the tunnel of the XRC System with the UVC lamps being turned on and the test samples being irradiated with UVC light for five seconds. The same procedure was again performed for *E. hirae*.

In order to determine the amount of bacteria in 2 control discs without UVC application and 3 test discs exposed to UVC irradiation for 5 seconds, the procedure was performed as described in the standard 13697+A1: 2019-09. For this purpose, dilutions of the harvest obtained from the surfaces were made and planted in petri dishes from the dilutions of −2, −3, −4, −5. For the test, dilutions of 0, −1, −2 and −3 were planted. They were incubated at 37° C.±1° C. for 1 day. After 1 day of incubation, counting was made. The log values of the bacteria recovered were calculated. Bactericidal (killing bacteria) activity was calculated in terms of log and % activity by comparing the mean log value of the control discs with the mean log value of the test discs.

Results:

TABLE 1

SURFACE DISINFECTION XRC CLEANBLUE ™ 75-55 CONVEYOR TYPE UVC BAGGAGE CLEANING SYSTEM - *S. aureus* (ATCC: 6538)

| Test Material | Density | Distance | LOG after 5 seconds | Lg reduction after 5 seconds | Result |
|---|---|---|---|---|---|
| SURFACE DISINFECTION "XRC CleanBlue 75-55" CONVEYOR TYPE UVC BAGGAGE CLEANING SYSTEM | — | — | 4.8 | R = Log K − Log T 8.31-4.8 | R = 3.51 (≥99.97%) |
| *S. aureus* Bacteria Control | | — | 8.31 | | |

TABLE 2

SURFACE DISINFECTION XRC CLEANBLUE ™ 75-55 CONVEYOR TYPE UVC BAGGAGE CLEANING SYSTEM - *E. hirae* (ATCC: 10541)

| Test Material | Density | Distance | LOG after 5 seconds | Lg reduction after 5 seconds | Result |
|---|---|---|---|---|---|
| SURFACE DISINFECTION "XRC CleanBlue 75-55" CONVEYOR TYPE UVC BAGGAGE CLEANING SYSTEM | — | — | 4.36 | R = Log K − Log T 8.21-4.36 | R = 3.85 (≥99.985%) |
| *E. hirae* Bacteria Control | | — | 8.21 | | |

XRC CLEANBLUE™ 75-55 CONVEYOR TYPE UVC BAGGAGE CLEANING SYSTEM, when applied for 5 seconds to surfaces contaminated with *S. aureus* (ATCC 6538) bacteria, demonstrated a 99.97% bactericidal (bacteria killing) effect.

XRC CLEANBLUE™ 75-55 CONVEYOR TYPE UVC BAGGAGE CLEANING SYSTEM, when applied for 5 seconds to surfaces contaminated with *E. hirae* (ATCC: 10541) bacteria, demonstrated a 99.985% bactericidal (bacteria killing) effect.

Example 2

Conveyor Type UVC Baggage and Cargo Disinfection System

The experiment was performed with an XRC CLEANBLUE™ 75-55 CONVEYOR TYPE UVC BAGGAGE CLEANING SYSTEM (the "XRC System"). The system contains a tunnel size of about 75 cm in width, about 55 cm in height, and about 150 cm length in total with an irradiation region of about 95 cm in length. The system contains 18 Osram® nominal 30 W UVC lamps of 90 cm in length emitting a dominant wavelength of 254 nm arranged in the following manner: four light bulbs in the top drawer, four light bulbs in the bottom drawer, and five light bulbs on each of the left and right drawers. The rollers of the XRC system operate at a speed that conveys objects through the tunnel at about 0.20 m/second. The total irradiation time in the tunnel of the XRC System is therefore about 5 seconds.

The bacteria being tested were *P. aeruginosa* (ATCC: 15442). The exposure time to UVC light was five seconds. The test environment was 23±2° C. The bacteria Incubation was 37° C.±1° C., 5% CO2.

Test Method:

Bacteria suspensions of *P. aeruginosa* were prepared using diluent and microorganism N number was determined by UV spectrophotometer. One control petri dish and two test petri dishes for of bacteria were prepared. The XRC System was operated for 5 minutes before testing and the UVC lamps were warmed up. The control petri dish containing *P. aeruginosa* bacterial sample was placed on the top of a platform having a height of about 20 cm (the platform being roughly the size and dimensions of a suitcase) and the test was carried out within the tunnel of the XRC System without the UVC lamps being turned. Then two test petri dishes containing *P. aeruginosa* bacterial samples were placed on the top of the same platform and the test was carried out within the tunnel of the XRC System with the UVC lamps being turned on and the test samples being irradiated with UVC light for five seconds.

In order to determine the amount of bacteria in the control dish without UVC application and 2 test dishes exposed to UVC irradiation for 5 seconds, the procedure was performed as described in the standard 13697+A1: 2019-09. For this purpose, dilutions of the harvest obtained from the surfaces were made and planted in petri dishes from the dilutions of −2, −3, −4, −5. For the test, dilutions of 0, −1, −2 and −3 were planted. They were incubated at 37° C.±1° C. for 1 day. After 1 day of incubation, counting was made. The log values of the bacteria recovered were calculated. Bactericidal (killing bacteria) activity was calculated in terms of log and % activity by comparing the mean log value of the control discs with the mean log value of the test discs.

Results:

TABLE 3

SURFACE DISINFECTION XRC CLEANBLUE ™ 75-55 CONVEYOR TYPE UVC BAGGAGE CLEANING SYSTEM - *P. aeruginosa* (ATCC: 15442)

| Test Material | Density | Distance | LOG after 5 seconds | Lg reduction after 5 seconds | Result |
|---|---|---|---|---|---|
| SURFACE DISINFECTION "XRC CleanBlue 75-55" CONVEYOR TYPE UVC BAGGAGE CLEANING SYSTEM | — | — | 3.48 | R = Log K − Log T 6.98-3.48 | R = 3.5 (≥99.96%) |
| *P. aeruginos* Bacteria Control | | — | 6.98 | | |

XRC CLEANBLUE™ 75-55 CONVEYOR TYPE UVC BAGGAGE CLEANING SYSTEM, when applied for 5 seconds to surfaces contaminated with *P. aeruginosa* (ATCC:15442) bacteria, demonstrated a 99.96% bactericidal (bacteria killing) effect.

Example 3

Conveyor Type UVC Baggage and Cargo Disinfection System

The experiment was performed with an XRC CLEANBLUE™ 75-55 CONVEYOR TYPE UVC BAGGAGE CLEANING SYSTEM (the "XRC System"). The system contains a tunnel size of about 75 cm in width, about 55 cm in height, and about 150 cm length in total with an irradiation region of about 95 cm in length. The system contains 18 Osram® nominal 30 W UVC lamps of 90 cm in length emitting a dominant wavelength of 254 nm arranged in the following manner: four light bulbs in the top drawer, four light bulbs in the bottom drawer, and five light bulbs on each of the left and right drawers. The rollers of the XRC system operate at a speed that conveys objects through the tunnel at about 0.20 m/second. The total irradiation time in the tunnel of the XRC System is therefore about 5 seconds.

The viruses being tested were Sars-Cov-2 (Covid-19) clinical isolate (GenBank: MT955161.1), Adenovirus Type 5 (Adenoid 75 strain), and Murine Norovirus (S99 Berline strain). The exposure time to UVC light was five seconds. The test environment was ambient temperature. The virus incubation was 37° C.±1° C., 5% CO2.

Test Method:

SARS-Cov-2 (Covid-19) clinical isolate (GenBank: MT955161.1), Adenovirus Type 5 (Adenoid 75 strain) and Murine Norovirus (S99 Berline strain) stock cultures were prepared using Vero E6, Vero and Raw Cell Lines, which were replicated with DMEM-10 (Dulbecco's Minimum Essential Medium with pen/strep/fungizone containing 10% FBS (fetal calf serum). The virus suspensions were dropped on a 2 $cm^2$ area on 304 2B stainless steel dishes specified in TS EN 16777:2019 standard and left to dry in a biosafety cabinet. Two control dishes and four test dishes were thus prepared for each virus being tested. While the control dishes were in the laboratory, the test dishes were placed atop a platform roughly sized and dimensioned like a suitcase with a height of about 20 cm and placed inside the tunnel of the XRC System as the XRC system was operated for five seconds. It was performed as described in the TS EN 16777:2019 standard to determine the amount of virus on the dishes exposed to UVC light for five seconds and the control which was not irradiated with UVC light. For this purpose, harvest obtained from the dishes was made to log dilutions and transferred to 96-well plates containing cells and incubated at 37° C.±1° C., 5% CO2 conditions. After four days of incubation, the cytopathic effect was evaluated under inverted microscope and the virus $TCID_{50}$ titer recovered was calculated according to the Spearman-Karber formula. Virucidal activity was calculated in terms of log and % activity by comparing the mean $TCID_{50}$ value of the control dishes with the mean $TCID_{50}$ value of the test dishes Results:

TABLE 4

SURFACE DISINFECTION XRC CLEANBLU ™ 75-55 CONVEYOR TYPE UVC BAGGAGE CLEANING SYSTEM, SARS-CoV-2 (Covid-19) Clinical isolate (GenBank: MT955161.1) Test Results

| TEST | Test Material | (Log $TCID_{50}$) | Average | Result | |
|---|---|---|---|---|---|
| Virus Titration | Stock Virus | 7.5 | — | R = Log K − Log T R = 5.58 | 99.9997% |
| Virucidal | Control Disc 1 | 6.17 | 6.08 | | |
| Test | Control Disc 2 | 6.00 | | | |
| (5 Seconds) | Test Disc 1 | 0.5 | 0.5 | | |
| | Test Disc 2 | 0.5 | | | |
| | Test Disc 3 | 0.5 | | | |
| | Test Disc 4 | 0.5 | | | |

TABLE 5

SURFACE DISINFECTION "XRC CLEANBLUE ™ 75-55 CONVEYOR TYPE UVC BAGGAGE CLEANING SYSTEM, Adenovirus Type 5 (Adenoid 75 strain) Test Results

| TEST | Test Material | (Log $TCID_{50}$) | Average | Result | |
|---|---|---|---|---|---|
| Virus Titration | Stock Virus | 8.00 | — | R = Log K − Log T<br>R = 4.70 | 99.9980% |
| Virucidal Test (5 Seconds) | Control Disc 1 | 5.83 | 5.58 | | |
| | Control Disc 2 | 5.33 | | | |
| | Test Disc 1 | 1.33 | 0.87 | | |
| | Test Disc 2 | 1.17 | | | |
| | Test Disc 3 | 0.5 | | | |
| | Test Disc 4 | 0.5 | | | |

TABLE 6

SURFACE DISINFECTION "XRC CLEANBLUE ™ 75-55 CONVEYOR TYPE UVC BAGGAGE CLEANING SYSTEM, Murine Norovirus (S99 Berlin strain) Test Results

| TEST | Test Material | (Log $TCID_{50}$) | Average | Result | |
|---|---|---|---|---|---|
| Virus Titration | Stock Virus | 7.5 | — | R = Log K − Log T<br>R = 4.83 | 99.9985% |
| Virucidal Test (5 Seconds) | Control Disc 1 | 5.50 | 5.41 | | |
| | Control Disc 2 | 5.33 | | | |
| | Test Disc 1 | 0.5 | 0.58 | | |
| | Test Disc 2 | 0.5 | | | |
| | Test Disc 3 | 0.5 | | | |
| | Test Disc 4 | 0.83 | | | |

XRC CLEANBLUE™ 75-55 CONVEYOR TYPE UVC BAGGAGE CLEANING SYSTEM, when applied for 5 seconds to surfaces contaminated with SARS-Cov-2 (Covid-19) Clinical isolate (GenBank: MT955161.1) virus, demonstrated a 99.9997% virusadal (virus killing) effect.

XRC CLEANBLUE™ 75-55 CONVEYOR TYPE UVC BAGGAGE CLEANING SYSTEM, when applied for 5 seconds to surfaces contaminated with Adenovirus Type 5 (Adenoid 75 strain) virus, demonstrated a 99.9980% virusidal (virus killing) effect.

XRC CLEANBLUE™ 75-55 CONVEYOR TYPE UVC BAGGAGE CLEANING SYSTEM, when applied for 5 seconds to surfaces contaminated with Murine Norovirus (S99 Berlin strain) virus, demonstrated a 99.9985% virusidal (virus killing) effect.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

I claim:

1. A baggage disinfection system forming a tunnel comprising:

a conveyor assembly comprising:

a frame with two or more supporting structures to support the frame and an opening on a side wall of the frame; and a series of rollers attached to the frame, wherein the rollers are spaced apart at a predetermined distance from one another;

a motor that operates the rollers and causes them to convey objects at a rate of between about 0.10 m/second and about 0.50 m/second from an entry end of the conveyor assembly to an exit end of the conveyor assembly;

a bottom drawer light bulb assembly that slides in and out of the opening on the side wall of the frame, said bottom drawer light bulb assembly having a base with at least one opening containing a cooling fan and further containing at least two ultraviolet light bulbs that are oriented in the bottom drawer light bulb assembly in a direction that is perpendicular to the rollers, wherein each light bulb emits light at a wavelength of between about 250 nm and about 260 nm, and wherein a removable wire mesh cover is disposed above the ultraviolet light bulbs and protects them from falling objects;

a tunnel frame connected to the conveyor assembly, the tunnel frame comprising a roof assembly and two opposing wall assemblies that together support the roof assembly, the roof assembly having a wire mesh extending across it, and each of the two opposing wall assemblies having a wire mesh that extend across each of the opposing wall assemblies, wherein each of the roof assembly and two opposing wall assemblies contain a gap that extend at least a part of the distance between an entry end of the tunnel frame and an exit end of the tunnel frame;

a top drawer light bulb assembly that slides in and out of the gap in the roof assembly, the top drawer light bulb assembly containing at least two ultraviolet light bulbs that are oriented in the top drawer light bulb assembly in a direction that is perpendicular to the rollers, wherein each light bulb emits light at a wavelength of between about 250 nm and about 260 nm, and wherein the light bulbs are disposed above the wire mesh extending across the roof assembly, wherein the wire mesh forms a protective barrier between the light bulbs and the tunnel itself;

a first side drawer light bulb assembly that slides in an out of the gap in the first of the two opposing wall assemblies, the first side drawer light bulb assembly containing at least two ultraviolet light bulbs that are oriented in said first side drawer light bulb assembly in a direction that is perpendicular to the rollers, wherein each light bulb emits light at a wavelength of between about 250 nm and about 260 nm, and wherein the light bulbs are disposed behind the wire mesh extending across the first opposing wall assembly, wherein the wire mesh forms a protective barrier between the light bulbs and the tunnel itself; and a second side drawer light bulb assembly that slides in and out of the gap in the second of the two opposing wall assemblies, the second side drawer light bulb assembly containing at least two ultraviolet light bulbs that are oriented in said second light bulb assembly in a direction that is perpendicular to the rollers, wherein each light bulb emits light at a wavelength of between about 250 nm and about 260 nm, and wherein the light bulbs are disposed behind the wire mesh extending across the second opposing wall assembly, wherein the wire mesh forms a protective barrier between the light bulbs and the tunnel itself;

wherein the baggage disinfection system is capable of inactivating at least 99.9% of a pathogen passing through the tunnel in less than or equal to about 30 seconds.

2. The baggage disinfection system of claim 1, wherein the pathogen is a coronavirus, an influenza virus, or a bacteria.

3. The baggage disinfection system of claim 2, wherein the pathogen is Sars-Cov-2 or a mutated version thereof.

4. The baggage disinfection system of claim 3, wherein the baggage disinfection system is capable of inactivating at least 99.9% of Sars-Cov-2 viruses or mutations thereof passing through the tunnel in less than or equal to about 10 seconds.

5. The baggage disinfection system of claim 3, wherein the baggage disinfection system is capable of inactivating at least 99.9% of Sars-Cov-2 viruses or mutations thereof passing through the tunnel in less than or equal to about 8 seconds.

6. The baggage disinfection system of claim 3, wherein the baggage disinfection system is capable of inactivating at least 99.99% of Sars-Cov-2 viruses or mutations thereof passing through the tunnel in less than or equal to about 30 seconds.

7. The baggage disinfection system of claim 3, wherein the baggage disinfection system is capable of inactivating at least about 99.99% of Sars-Cov-2 viruses or mutations thereof passing through the tunnel in less than or equal to about 10 seconds.

8. The baggage disinfection system of claim 3, wherein the baggage disinfection system is capable of inactivating at least about 99.99% of Sars-Cov-2 viruses or mutations thereof passing through the tunnel in less than or equal to about 8 seconds.

9. The baggage disinfection system of claim 1, wherein each of the light bulb assemblies contain at least 4 UVC emitting light bulbs.

10. The baggage disinfection system of claim 1, wherein the system contains at least sixteen UVC emitting light bulbs.

11. The baggage disinfection system of claim 1, wherein the system contains at least eighteen UVC emitting light bulbs.

12. The baggage disinfection system of claim 1, further comprising an ozone sensor that issues a signal if the amount of ozone detected is in excess of an acceptable limit of ozone emission.

* * * * *